United States Patent [19]

Baillie

[11] Patent Number: 4,813,270
[45] Date of Patent: Mar. 21, 1989

[54] SYSTEM FOR MEASURING MULTIPHASE FLUID FLOW

[75] Inventor: Lloyd A. Baillie, Plano, Tex.

[73] Assignee: Atlantic Richfield Company, Los Angeles, Calif.

[21] Appl. No.: 163,930

[22] Filed: Mar. 4, 1988

[51] Int. Cl.$^4$ .............................................. G01N 25/18
[52] U.S. Cl. ....................................... 73/61 R; 374/33
[58] Field of Search .................. 73/61 R, 61.1 R, 155; 374/31, 33

[56] References Cited

U.S. PATENT DOCUMENTS

| | | | |
|---|---|---|---|
| 3,712,116 | 1/1973 | Andre | 73/61.1 R X |
| 4,720,998 | 1/1988 | Hogue | 73/61 R X |

Primary Examiner—Jerry W. Myracle
Attorney, Agent, or Firm—Michael E. Martin

[57] ABSTRACT

Water, oil and gas mixtures such as produced from oil and gas wells are analyzed as to the proportionate content of each component in the total mixture by calorimetric processes in systems which separate the gas from the fluid mixture, withdraw a sample of the liquid mixture and subject the sample at a given or determined flow rate to a heat exchange process. The remaining main flow of the liquid mixture is also subjected to a heat exchange process and a heat balance is calculated for the flowstream based on the change in temperature of main liquid flowstream and the change in temperature of the heat exchange medium. The processes are carried out on the main flowstream by interposing a heat exchanger in the flowstream or by reinjecting into the flowstream a measured amount of heat exchange fluid such as separated water or crude oil. The components of the liquid portion of the flowstream may be analyzed by passing a liquid sample through a heat exchanger to measure the heat loss or increase of the sample together with mass flow and volumetric flowmeters or by passing the liquid sample flowstream through a source of microwave electromagnetic energy and measuring the dielectric properties of the fluid mixture.

29 Claims, 5 Drawing Sheets

4,813,270

SYSTEM FOR MEASURING MULTIPHASE FLUID FLOW

BACKGROUND OF THE INVENTION

1. Field of the Invention

The present invention pertains to systems and methods for measuring multiphase fluid flow, particularly combined flows of crude oil, water and gas produced from a hydrocarbon bearing formation. The systems use calorimetric liquid phase measurement techniques combined with density measurement and measurements based on the dielectric properties of a multicomponent liquid.

2. Background

There are several process and transport applications wherein the flow rates of the components of a multiphase fluid must be determined. One particularly vexatious application is in regard to the production of well fluids from a subterranean hydrocarbon bearing formation. The accurate determination of the amounts of the respective component in a mixture, primarily comprising oil, water and gas, is important from an economic and regulatory standpoint, in particular. Moreover, the requirements for measuring the flow from a well or a combined flowstream from several wells using prior art methods may be aggravated by space requirements in certain locations, such as offshore production platforms and liquid gathering and processing systems operating in adverse climates such as Arctic regions.

It is also important that a sample be measured which is representative of the full flowstream of fluid being produced and transported so as to avoid errors associated with conventional methods for measuring so-called slipstream samples. It is also desirable that the flow measuring apparatus be reliable and not subject to measurement errors when operating at conditions wherein the fluids being monitored may be a high percentage of one phase at a particular time and then go through a substantial change in the makeup of the fluid stream. Certain oil producing formations are subject to such wide variations in the flow of water, oil and gas, respectively, as the formation is produced.

With these problems and desiderata apparent in the art of multiphase flow measurement, there has been a continuing effort to develop systems and methods for measuring multiphase fluid flow. The present invention provides systems and methods which are believed to be advantageous and solve many of the problems mentioned herein, as well as overcoming deficiencies of prior art systems and methods.

SUMMARY OF THE INVENTION

The present invention provides an improved system for measuring multiphase fluid flow, particularly flows involving at least two liquids of different composition and a gas phase, all mixed together. In particular, the system of the present invention is well suited for measuring the respective components of fluid flowstreams produced from oil and gas wells and the like.

In accordance with an important aspect of the present invention, systems are provided for measuring multiphase fluid flow which may be interposed in the main fluid flowstream leading from a source to a destination of the multiphase fluid. In particular, the systems provide for liquid samples to be continuously or at least frequently withdrawn from the main flowstream, separated from the gas phase and reinjected into the main flowstream without interruption of the flowstream.

In accordance with one embodiment of the present invention, a multiphase flowstream of gas and liquids of different composition, such as water and crude oil, is separated into liquid and gas phases and the liquid phase is subjected to a heat exchange process with a stream of cooling liquid of known flow rate and wherein the specific heats of the water and crude oil in the flowstream are assumed to be known. The volumetric fraction of crude oil in the liquid is derived from relationships between the specific heats of the water and oil in the combined flowstream. Volumetric flow rates are obtained from heat balance relationships.

In accordance with another embodiment of the present invention, the volumetric flow rate of liquid in the flowstream, together with the oil and water fraction, is determined by heat balance relationships which are carried out utilizing injection into the flowstream of known quantities of oil or water or passing the flowstream through a heat exchanger. A liquid sample of known flow rate is subjected to a heat exchange process of measured heat input. The mean specific heat of the liquid mixture is monitored and utilized in determining the volumetric fraction of oil and water. Alternatively, a liquid sample, withdrawn from the flowstream, may be passed through a device which determines the relative amounts of oil and water from microwave radiation transmissivity characteristics.

The superior features and advantages of the systems and methods of the present invention will be further appreciated by those skilled in the art upon reading the detailed description which follows in conjunction with the drawing.

DESCRIPTION OF PREFERRED EMBODIMENTS

Figure 1:
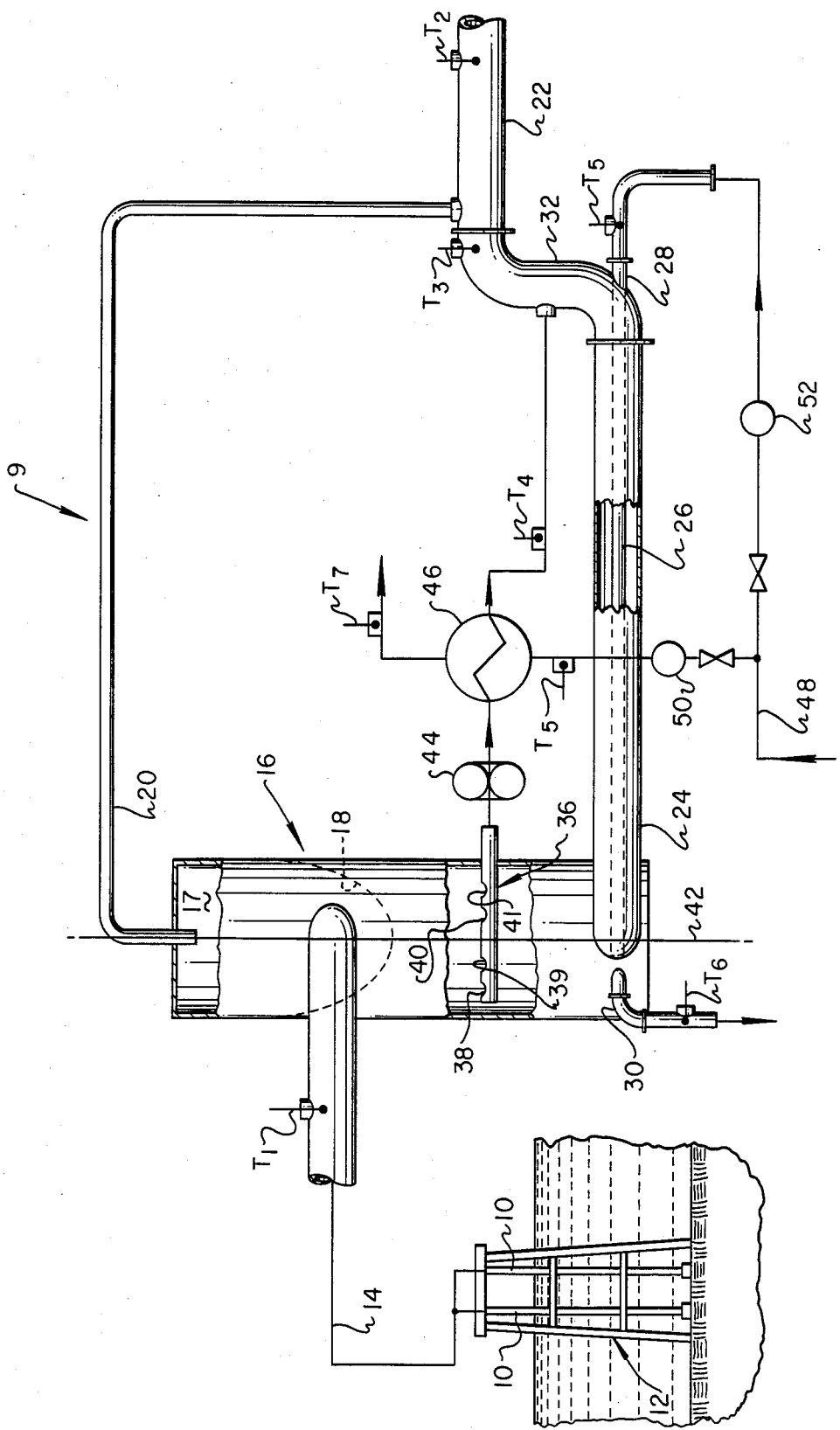
FIG. 1 is a schematic diagram of a system for measuring the flow rates of the components of a multiphase fluid flowstream.

In the description which follows, like parts are marked throughout the specification and drawing with the same reference numerals, respectively. The drawing figures are not necessarily to scale and most of the components are shown in somewhat schematic form in the interest of clarity and conciseness.

Referring to FIG. 1, there is illustrated a system 9 for measuring the flow rates of the components of a multiphase fluid flowstream, such as may typically be produced from subterranean wells which have been completed to produce fluids through risers 10 connected to a conventional offshore oil production platform 12. The production risers 10 are suitably connected to a flow line or produced fluids conduit 14. Samples of the components of the fluid flowstreams being produced through the risers 10 may be obtained periodically and analyzed to determine the composition of each fluid in the flowstream. However, typically the flowstream comprises primarily three components: crude oil, water and natural gas. In the embodiment illustrated in FIG. 1, the produced fluids conduit 14, which may lead to an offshore or onshore processing system, not shown, is connected to a vapor-liquid separator 16 comprising a generally cylindrical vessel having a diameter preferably at least twice the diameter of the conduit 14. The conduit 14 forms a tangential inlet to the interior of the separator 16 so that a vortical flow of fluid is produced which will separate substantially all of the vapor from liquid to form an interface 18. Vapor is drawn off from the interior space 17 of the separator 16 through a vapor conduit 20 and rejoins the liquid mixture at a point downstream of the separate in a continuation of the produced fluids conduit designated by the numeral 22.

The conduit 22 includes a generally horizontally extending portion 24 which may be approximately five to six feet in length and which forms a tangential outlet from the bottom of the separator 16 for conducting a liquid mixture separated within the separator therefrom. The conduit section 24 preferably includes heat exchanger conduit means 26 extending centrally therethrough and entering the conduit section 24 at a fitting 28 and exiting the conduit section through a fitting 30 formed in the sidewall of the separator 16. The conduit means 26 may include multiple tubes or tubes with heat exchange surfaces thereon, if needed. The produced fluids conduit section 24 is connected to the conduit 22 through a conduit section 32 having two right angle elbow portions arranged such that the conduit 22 is elevated at least about two feet above the conduit section 24 and is at least one foot below the point of connection between the conduit 14 and the separator 16. This overall arrangement of the separator 16 and the conduits leading to and from the separator provides for separation of the vapor or gas from the multiphase fluid flowstream so that they flow through separate paths for a distance of only a few feet.

The liquid flowing through the separator 16 from the conduit 14 to the conduit section 24 passes downward over a liquid withdrawal tube 36 which preferably extends across the diameter of the cylindrical separator vessel and has a series of spaced apart inlet ports 38, 39, 40 and 41, for example. The distribution of the inlet ports 38 through 41, which are spaced radially from the central longitudinal axis 42 of the vessel 16, provides for withdrawal of a suitably representative sample of the liquid mixture. The sample liquid stream withdrawn from the separator 16 through the tube 36 is transferred through a pump 44 of known pumping rate to a heat exchanger 46 and returned to the main liquid flowstream at the conduit section 32, as illustrated. The heat exchanger 46, which may be of a shell and tube type, is provided with cooling water from a source, not shown, by way of a conduit 48 and a flowmeter 50. Cooling water passes through the heat exchanger 46 and is discharged to a suitable point, not shown. The same water source is adapted to supply cooling water to the heat exchanger conduit 26 by way of conduit 48 and a flowmeter 52.

The various fluid streams conducted through the system illustrated in FIG. 1 are monitored by temperature sensors which bear the designations used in the equations set forth hereinbelow. The temperature of the multiphase fluid flowstream entering the separator 16 and prior to any heat exchange is designated by the reference numeral $T_1$, the temperature of the fluid stream leaving the system illustrated is $T_2$, the temperature of the liquid flowstream before remixing with the separated vapor is $T_3$, the temperature of the sample liquid mixture after heat exchange in the heat exchanger 46 is indicated at $T_4$, the cooling water inlet temperatures to both heat exchangers 26 and 46 are $T_5$, and the respective cooling water exit temperatures from the heat exchangers 26 and 46 are $T_6$ and $T_7$, respectively.

Preferably, the temperature of the cooling water entering the heat exchangers 26 and 46 is at least 30° F. below the average temperature of the fluid stream entering the system from the conduit 14. The flow rates of cooling water are monitored by the flowmeters 50 and 52 so that these values are known for use in the equations stated hereinbelow. By monitoring the inlet and outlet temperatures of both the sample liquid flowstream passing through the conduit 36 and the multiphase stream passing through the system, illustrated in FIG. 1, the fraction of water in the liquid and the average specific heat of the liquid may be determined.

For example, a volumetric flow rate heat balance equation may be written for the cooling water flow and the volumetric flow rate of the liquid sample passing through the heat exchanger 46 using the equation:

$$F_{wa}C_w(T_7-T_5)=F_{La}C_L(T_1-T_4) \qquad (1)$$

wherein $F_{wa}$ is the volumetric cooling water flow rate through the heat exchanger 46, $C_w$ is the volumetric specific heat of water, $F_{La}$ is the volumetric flow rate of the liquid sample passing through the heat exchanger 46 and $C_L$ is the liquid volumetric specific heat, which is also the product of the mass specific heat and density of the liquid sample. Accordingly, solving for $C_L$:

$$C_L = \frac{F_{wa}(T_7 - T_5)}{F_{La}(T_1 - T_4)} = X_oC_o + (1 - X_o)C_w \qquad (2)$$

Wherein $X_o$ is the volumetric fraction of oil in the liquid, $C_o$ is the product of oil density and oil specific heat (or volumetric specific heat) and $C_w$ is the product of water density and water specific heat (or volumetric specific heat), therefore, solving for a value of $X_o$:

$$X_o = \frac{C_w - C_L}{C_w - C_o} \qquad (3)$$

Still further, the flow rate of the cooling water passing through the heat exchanger 26 is indicated by the reference numeral $F_{wb}$ and the combined effects of these streams is measured at the temperature sensor $T_3$ wherein the total liquid flowrate $F_L$ can be found from the equation:

$$F_L = \frac{C_w}{C_L} \cdot \frac{F_{wa}(T_7 - T_5) + F_{wb}(T_6 - T_5)}{(T_1 - T_3)} \qquad (4)$$

and the volumetric oil flow rate will be:

$$F_o = X_o \times F_L \qquad (5)$$

Moreover, the partially cooled liquid stream is joined by the uncooled vapor stream between temperature sensors $T_3$ and $T_2$. Accordingly, a heat balance across these points may be written as:

$$F_L C_L (T_2 - T_3) = F_v C_p (T_1 - T_2) \tag{6}$$

where $C_p$ is the specific heat of the vapor or gas in the flowstream. The flow rate of vapor, $F_v$ is then:

$$F_v = F_L \frac{C_L(T_2 - T_3)}{C_p(T_1 - T_2)} \tag{7}$$

Accordingly, the flow rates of the components of the liquid mixture comprising water, oil and vapor or gas may be determined solely using calorimetric processes and by withdrawing only a small sample of liquid on a continuous basis from the multiphase fluid stream. The system illustrated in FIG. 1 is well suited to be interposed in a main fluid conduit for conducting a multiphase fluid mixture from a source such as a well providing one or a combination of liquid and gaseous hydrocarbons.

Figure 2:
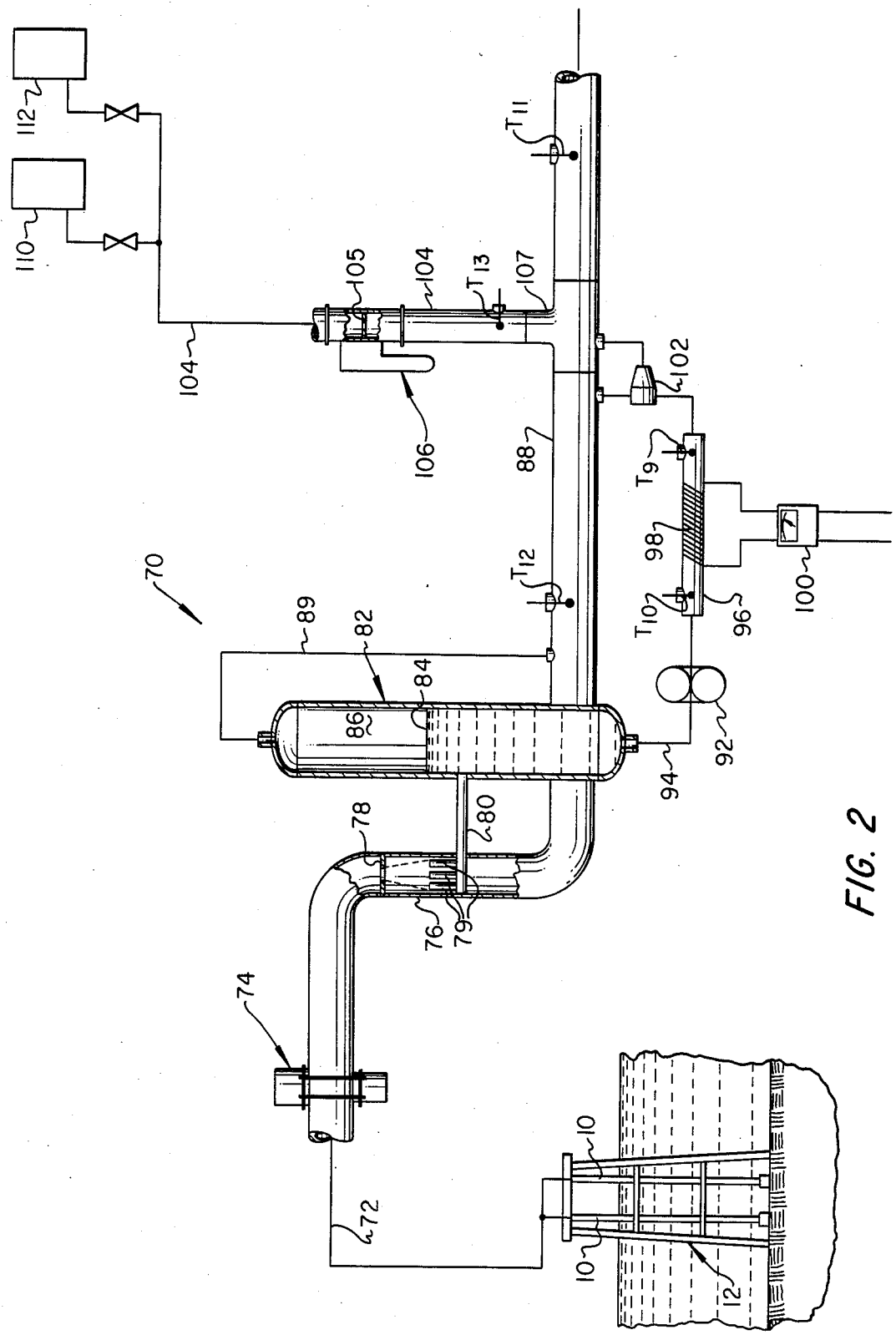
FIG. 2 is a schematic diagram of one alternate embodiment of a system in accordance with the present invention.

Referring now to FIG. 2, another embodiment of the present invention which uses calorimetric techniques to determine the components of a mixture of liquids and gases from a hydrocarbon reservoir, for example, is illustrated and generally designated by the numeral 70. The system 70 includes a conduit 72 connected to the production risers 10 for conducting a multiphase fluid flowstream of known component composition, respectively, such as crude oil, water and natural gas or other hydrocarbon vapors.

The conduit 72 is fitted with a densitometer 74 which may be of a commercial type operating on a gamma ray absorbtion principle. One type of densitometer commercially available is a type SGD Digital Density System manufactured by Texas Nuclear of Austin, Tex., USA. The densitometer 74 is adapted to measure the overall average density of a fluid mixture being conducted through the conduit 72.

The conduit 72 includes a downwardly extending column portion 76 having a flow restricting orifice plate 78 interposed therein and providing an orifice for generating a uniformly dispersed spray of fluid downwardly through the column portion 76. An array of Pitot tubes 79 is disposed across the diameter of the column portion 76. Each of the Pitot tubes 79 is connected to a conduit 80 leading to a liquid-vapor separator vessel 82. The conduit 80 enters the separator vessel 82, preferably below a liquid level line 84. Fluid in the vessel 82 is allowed to separate into vapor and liquid phases and vapor collects in a chamber 86 for reinjection into the main conduit of the system 70 through a conduit 89 as illustrated.

The system 70 includes a heat exchanger portion of the main conduit 72, designated by the numeral 88. Vapor separated from the liquid flowstream in the vessel 82 re-enters the flowstream along the conduit section 88 at a point sufficiently downstream so that a pressure differential is created which promotes the flow of vapor from the chamber 86 by way of conduit 89 back into the conduit section 88. Liquid collected in the separator vessel 82 is pumped at a known constant rate through a metering pump 92 interposed in a conduit 94 and through a heat exchanger 96 which is provided with a controlled, and constant heat input type of heater 98. The heater 98 may be an electrical resistance type having a suitable power meter 100 interposed in its circuitry for monitoring the rate of heat input to the heat exchanger 96 from an electrical source, not shown. The temperature increase of the fluid sample being pumped through the heat exchanger 96 is measured by the temperature sensors $T_9$ and $T_{10}$. A pressure regulator valve 102 is preferably provided in the return line of the liquid sample to maintain a pressure in the heat exchanger 96 of about 20 psig above the main fluid stream pressure to prevent vaporization of the liquid while it is passing through the heat exchanger 96.

The total heat capacity of the flowstream being conducted through the heat exchanger section 88 is determined by injecting a stream of water or oil of accurately measured flow rate and temperature. In certain applications, as described herein, a conventional shell and tube heat exchanger may be desirable for determining the heat capacity measurement. Alternative, and in some applications advantageously, the injection of the premeasured rate of water or oil directly into the flowstream avoids the space and weight considerations required for a heat exchanger and neither of these substances present any particular problem in being injected into the flowstream since they are already present in the flowstream.

As illustrated in FIG. 2, water or oil may be injected into the heat exchanger section 88 between temperature sensors $T_{11}$ and $T_{12}$ through a conduit 104 which is connected to the conduit section 88 at a tee fitting 107. An orifice plate 105 comprising part of a flowmeter 106 is interposed in conduit 104 and a temperature sensor $T_{13}$ is provided for measuring the temperature of the liquid being injected into the flowstream. A source of water 110 and a source of oil 112 may be selectively connected to the conduit 104 for injection at a premeasured rate into the main conduit heat exchanger section 88. The source of oil 112 may be previously separated crude oil which has been processed after discharge from the system 70. The use of oil may be preferred to avoid a high water content of the flowstream.

It is possible to determine the volumetric fraction of total flow which is liquid from empirical analysis in horizontal tubular conduits. The volumetric fraction of liquid flow, $\beta$ is:

$$\beta = \text{liquid flow}/(\text{liquid flow} + \text{vapor flow}). \tag{8}$$

In horizontal tubes, $\beta$ may be determined by the following correlation. In mixed phase flow through 0.50 inch diameter horizontal tubes:

$$\beta = 1.57(\alpha - \theta)^{2.5} + \theta, \text{ where}$$
$$\theta = 0.5(\alpha - 0.74 + |\alpha - 0.74|). \tag{9}$$

This empirical relationship can be derived from a logarithmic-logarithmic plot. The constant $\alpha$ may be derived from the equation:

$$\alpha = \frac{d - d_V}{d_L - d_V} \tag{10}$$

wherein d is the average density of the flowstream as measured by the densitometer 74, $d_L$ is liquid density and $d_V$ is gas or vapor density. The liquid density and gas density may be determined from periodic sample analysis and by monitoring flowstream pressure and temperature conditions.

The basis of the above correlation is believed to reside in the fact that liquid velocities are lower than gas velocities in a substantially horizontal conduit except when the conduit, in the form of a circular pipe, is more than about 75% full of liquid as measured across the diameter of the pipe. When the pipe is more than 75% full of liquid, the gas or vapor is present as bubbles in the liquid and the bubbles move with the same average velocity as the liquid. When the pipe is less than 75% full of liquid, the ratio of liquid velocity to vapor velocity becomes progressively smaller as the ratio of liquid to vapor volume in the conduit becomes smaller.

Moreover, the constant $\beta$ may be determined by an iterative process as a function of the specific heat of the combined flowstream, and using an initial valve of $\beta = 1$. The equation used for iteration is:

$$C = \frac{\beta d_L C_L + (1 - \beta) d_v C_v}{\beta d_L + (1 - \beta) d_v} \quad (11)$$

The volumetric fraction of oil in a water-oil liquid mixture may be determined from the following equation:

Volumetric Fraction of
Oil $= RD - kW/RD(C_w - C_o)$ (12)

wherein R is the volumetric rate of pumping by the pump 92, D is the temperature differential $T_9 - T_{10}$, and $C_w$ and $C_o$ are the volumetric specific heats of water and oil, respectively. The constant k is equal to 0.43 if W is the input power in watts to heater 98, and R is in ml/sec., temperatures are in °F. and the volumetric specific heats are in cal./ml/°F. Still further, the average liquid specific heat may be determined by the equation:

$$C_L = kW/RD. \quad (13)$$

The specific heat of the stream flow is predominantly due to the liquid flow and the volumetric liquid flow rates $F_o$ and $F_w$ for oil and water, respectively, are primarily affected by the accuracy of an overall heat capacity determination and by the accuracy of the mean liquid specific heat, $C_L$. The vapor or gas flow rate is affected by the accuracy of the total liquid flow rate and by the reliability of the correlation which relates gas to liquid flow ratios and gas to liquid volume ratios in the stream conduit. Under most operating conditions of handling mixtures of crude oil, water and gas, it is believed to be possible to achieve a range of plus or minus 2% accuracy on oil and water flow rates and about plus or minus 5% accuracy on gas flow rates.

The following equations are useful for determining volumetric liquid flow rates ($F_L$), the volumetric oil flow rate ($F_o$), the volumetric water flow rate ($F_w$) and the volumetric gas or vapor flow rate ($F_v$) where $F_{cw}$ is the volumetric flow rate of cooling water (or cooling oil) injected into the flowstream:

$$F_L = \frac{F_{cw} C_w (T_{11} - T_{13}/(T_{12} - T_{11})}{C_L + C_v(1/\beta - 1)} \quad (14)$$

$$F_o = F_L \frac{C_w - C_L}{C_w - C_o} \quad (15)$$

$$F_w = F_L \frac{C_L - C_o}{C_w - C_o} \quad (16)$$

$$F_v = F_L(1/\beta - 1) \quad (17)$$

Figure 3:
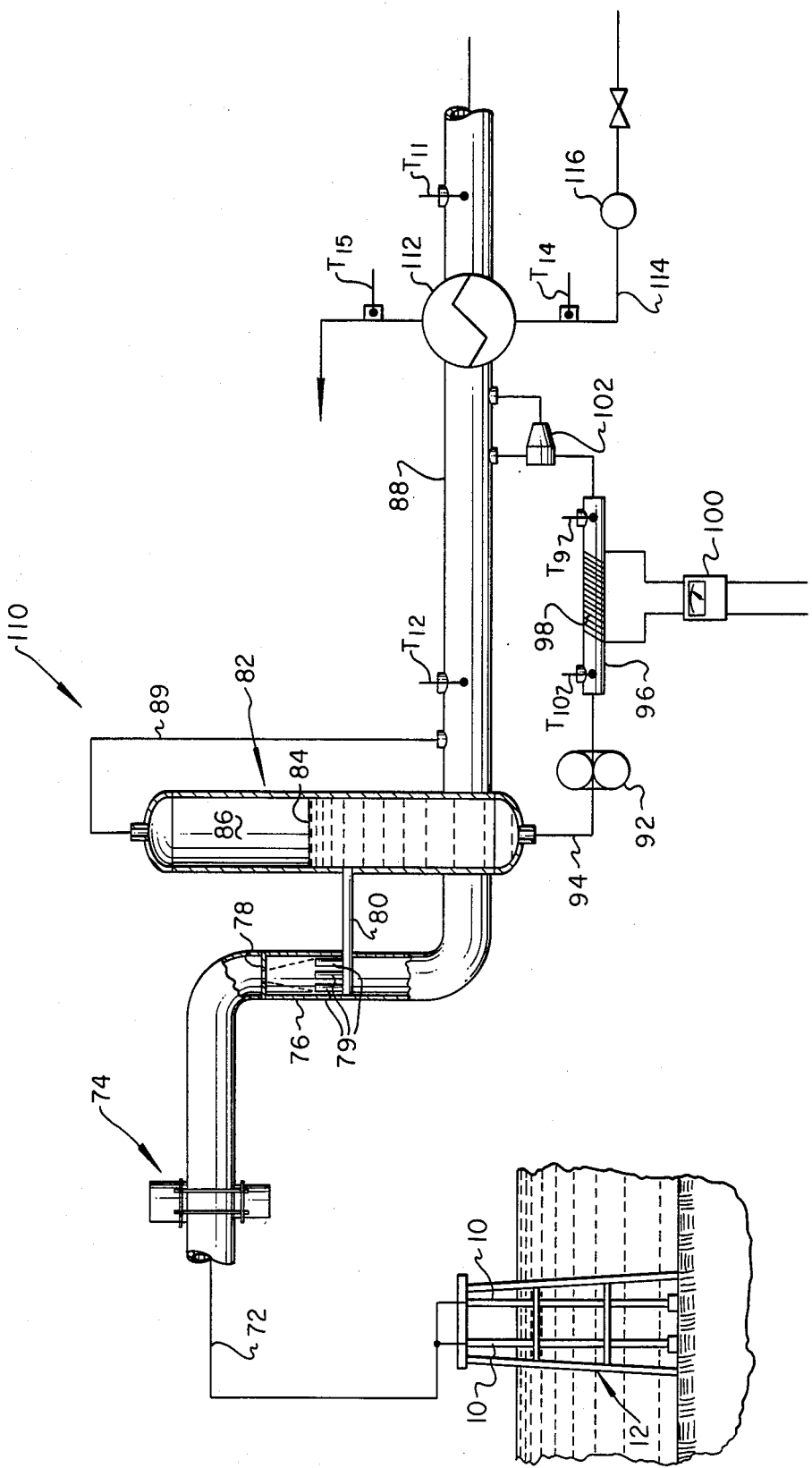
FIG. 3 is a schematic diagram of a second alternate embodiment of a system in accordance with the present invention.

Referring now to FIG. 3, there is illustrated a second alternate embodiment of a calorimetric flow measurement system in accordance with the present invention. The system illustrated in FIG. 3 is generally designated by the numeral 110 and is similar to the system 70 except for the replacement of the liquid injection conduit 104 and flowmeter 106 with a heat exchanger 112 interposed in the conduit section 88. The heat exchanger 112 may be of a shell and tube type with the well fluid flowstream passing through the tube side of the exchanger. Cooling water is supplied from a source, not shown, through a conduit 114 and a flowmeter 116. The flowmeter 116 determines cooling water flow rate ($F_{cw}$). The temperature differential of the cooling water flow is determined from temperature sensors $T_{14}$ and $T_{15}$. The equations (8) through (17) may be used to determine the respective flow rates. In equation (14), the temperature difference $T_{15} - T_{14}$ is substituted for the temperature difference $T_{11} - T_{13}$.

The decision on selecting a heat exchanger, such as the exchanger 112, versus direct injection of water or oil into the well effluent flowstream may depend on well flow rates, space available and cooling liquid availability. For example, consider a well or other source of multiphase fluid flow having a total liquid output of about 10,000 barrels per day, of which 50% is water, and wherein the volumetric flow ratio of gas to liquid is about 10 to 1 at wellhead conditions. The mean specific heat is 0.7 BTU's/lb.°F. at 300 lbs. per barrel and total flow is about 125,000 lbs. per hour. If the flowstream is to change temperature by about 5° F., then 437,500 BTU's per hour will be needed to be exchanged. For an average tube to shell temperature differential of 50° F. and cooling water inlet to outlet differential of 20° F., the cooling water flow rate will be required to be about 21,875 lbs. per hour or 43.7 gallons per minute. Calculation of the heat transfer rate of the shell and tube type heat exchanger indicates that approximately 219 square feet of tube surface area will be required. This can be provided by a tube bundle of about 18.25 feet in length by 9.0 inches in diameter containing an array of sixty-one 0.750 inch diameter tubes. Tube area and shell area would both be about 0.225 sq. ft. so that tube velocities would be about 32 feet per second and shell velocities would be about 0.43 feet per second. Wells with producing rates less than 10,000 barrels per day would require smaller exchangers, usually less than about 10.0 feet in length.

Alternatively, if water is injected directly into the wellhead flowstream, such as in the system illustrated in FIG. 2, with the same well flow conditions, the required amount of cooling water would be reduced from 43.7 gallons per minute to 17.5 gallons per minute, assuming a 5° F. change in the flowstream temperature and a 50° F. change in the cooling water temperature. The total mass flow of the multiphase fluid flowstream from the well system would increase by a factor of 1.07 and the water fraction of liquid would increase from the assumed 50% to 53.3%. If wellhead pressure is assumed to be 1000 psig, the required power for injecting a stream of cooling water would be about 10.2 hp or about 1.0 hp for each 1000 barrel per day of production. Moreover, if the water content of the well production stream is reduced to only 10% of liquid flow, for example, then the required heat exchange would be reduced to approximately 11.5 gallons per minute and requiring only 6.7 hp for pumping. The advantages of a water injection system reduce the cost and bulk of the wellsite equipment and simplify the problem of sizing the system to match the output of the well. However, the additional water injection might be objectional in certain separating systems. Alternatively, of course, as indicated previously, separated crude oil could be cooled and returned to the system for use as the heat exchange fluid injected into the flowstream.

Figure 4:
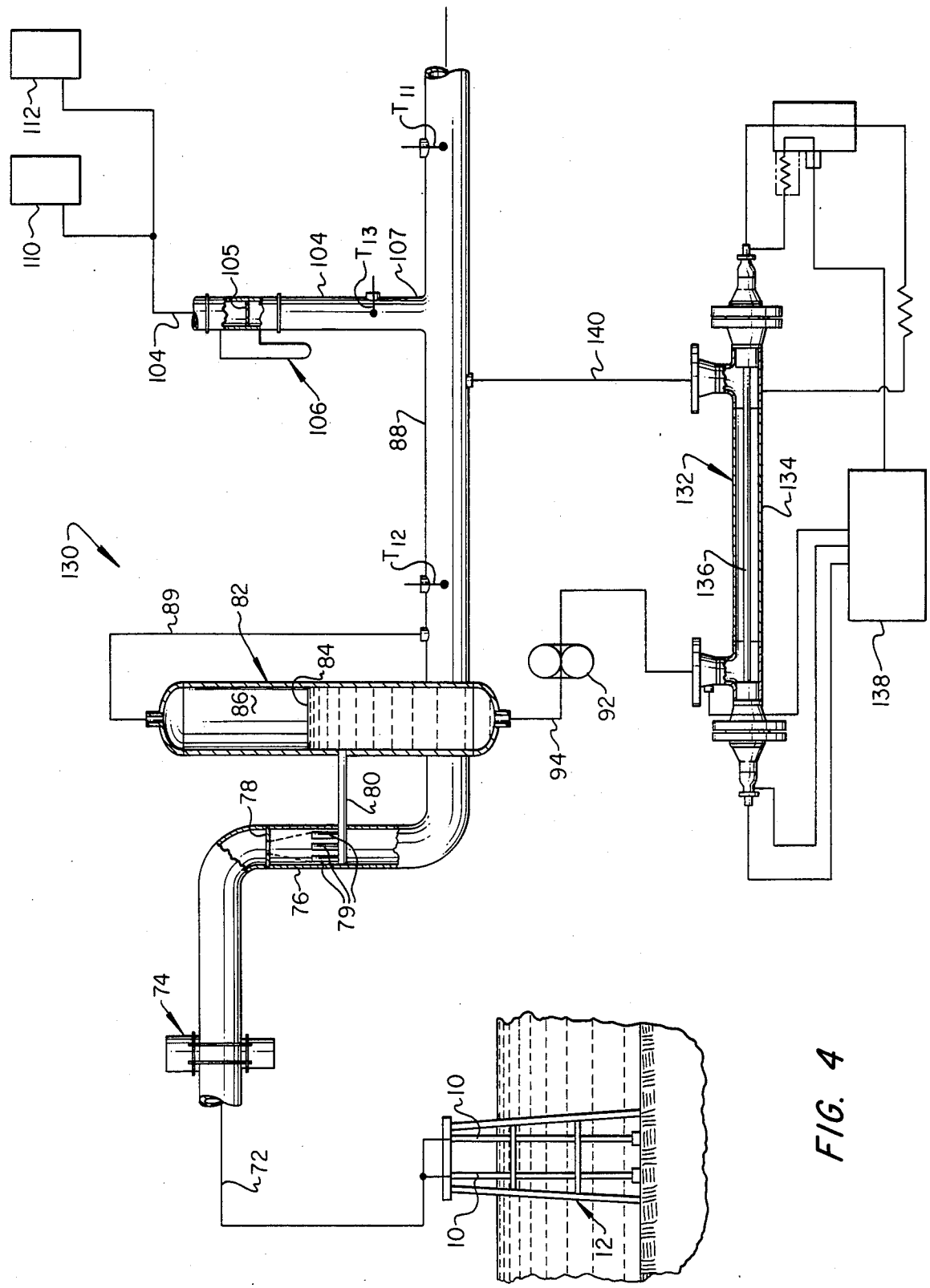
FIG. 4 is a schematic diagram of a third alternate embodiment of a system in accordance with the present invention.

Referring now to FIG. 4, a third alternate embodiment of a system in accordance with the present invention is illustrated and generally designated by the numeral 130. The system 130 is similar to the system 70 except that the heat exchanger 96 for determining the ratio of water to oil in the liquid stream is replaced by an apparatus 132 comprising a conduit 134 for receiving and discharging a continuous flowstream of liquid mixture. The conduit 134 is formed as part of a coaxial microwave transmission line, including a center conductor 136. A microwave or radio frequency range signal generator and recording circuit 138 is operably connected to the apparatus 132 and preferably includes an unbuffered oscillator for generating a high frequency signal which may be varied by a voltage controlled oscillator tuning circuit, not shown. A signal receiver circuit, not shown, monitors the change in frequency and transmits a differential frequency signal to a suitable frequency counter for comparison of the measured signal with known reference signals for determining the percentage of one liquid mixed with the other in the flowstream passing through the conduit 134. The apparatus 132 is described in greater detail in copending U.S. patent application Ser. No. 932,068 filed Nov. 16, 1986 and assigned to the assignee of the present invention.

Accordingly, the fraction of water in the water-oil mixture being reinjected by way of the conduit 140 into the main conduit section 88 may be determined by the apparatus 132 in place of utilizing a thermal or calorimetric arrangement as provided in the embodiments of FIGS. 1 through 3. This particular arrangement is advantageous for systems wherein a relatively low percentage of water in oil is expected over the range of composition of the fluids flowing from the well system.

Figure 5:
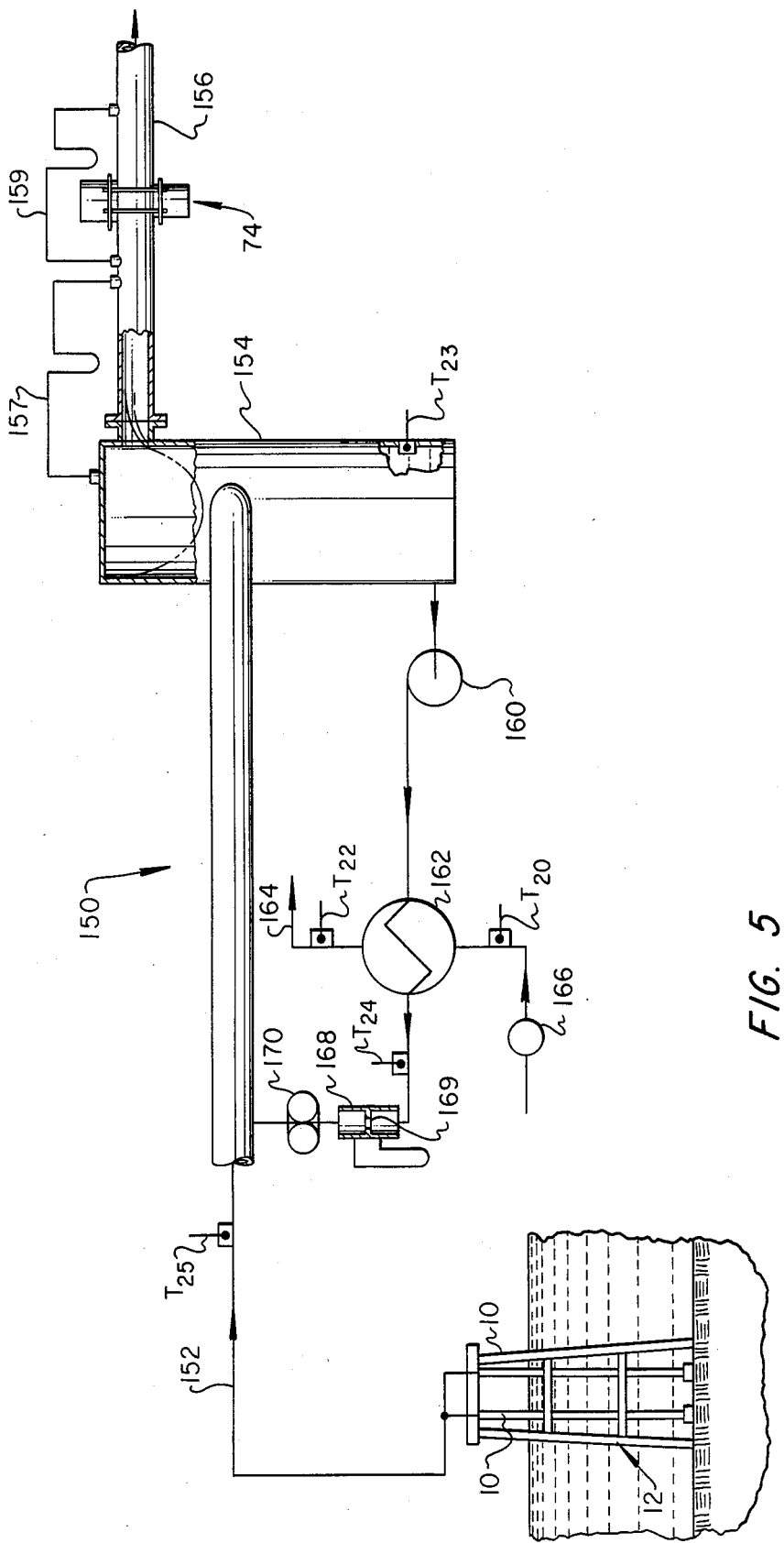
FIG. 5 is a schematic diagram of a fourth alternate embodiment of the invention.

Referring now to FIG. 5, a fourth alternate embodiment of a system for measuring multi-phase fluid flow is illustrated and generally designated by the numeral 150. The system 150 includes a main supply conduit 152 for conducting a flow of fluid from a source such as the risers 10 comprising oil, water and gas and wherein the oil and gas are of substantially known composition. In the system 150 the conduit 152 terminates in a separator 154 wherein a portion of the liquid phase of the fluid is disengaged from the gas at least temporarily but then re-enters the flow stream and leaves the separator through a conduit 156 along with the previously separated gas.

The separator 154 is primarily intended to provide a source of degassed liquid which is conducted by way of a pump 160 through a heat exchanger 162 having cooling water supplied through a conduit 164 and of known flow rate measured by a flowmeter 166. Liquid leaves the heat exchanger 162 and flows through an orifice type flowmeter 168 and may also be conducted through a positive displacement type or turbine type flowmeter 170 wherein the liquid re-enters the main flow stream being conducted through the conduit 152. Temperatures are measured in the system 150 as indicated in the diagram of FIG. 5 wherein $T_{20}$ is the cooler water inlet temperature and $T_{22}$ is the cooling water outlet temperature from the heat exchanger 162. The temperature $T_{23}$ is the equilibrium temperature of the liquid after remixing of the sample flowstream with the main flowstream and before heat exchange with the cooling water, $T_{24}$ is the liquid temperature after heat exchange with the cooling water and $T_{25}$ is the temperature of the main flowstream before joining the recycled liquid sample flowstream which is conducted through the heat exchanger 162.

It is possible to calculate the mass flow rate of a fluid stream from pressure differentials across an orifice meter plus knowledge of the volumetric flow rate without knowing density. For example, the mass flow rate M may be determined from the equation;

$$M = 2gA^2 \Delta P / F \qquad (18)$$

Wherein g is the gravitational constant, A is the cross sectional area of the orifice of the orifice flowmeter such as the cross sectional area of the orifice 169 of the orifice flowmeter 168, $\Delta P$ is the pressure differential across the orifice flowmeter and F is the volumetric flow rate.

With the mass flow rate known, it is possible to find the weight fraction of oil in the liquid by measuring the temperature across the heat exchanger 162 since the volumetric flow rate of cooling water $F_{cw}$, the specific heat of oil $C_o$ and the specific heat of water $C_w$ are known quantities. The weight fraction X of oil in the liquid sample flowstream flowing through the heat exchanger 162 can be determined from the following equation:

$$X = \frac{C_w}{C_w - C_o} \cdot \left(1 - \frac{(T_{22} - T_{21})F_{cw}}{(T_{23} - T_{24})M}\right) \qquad (19)$$

When the sample liquid stream joins the main flow stream in the conduit 152, both streams will come to a common temperature $T_{23}$. A heat balance may be calculated where $F_L$ is the liquid volumetric flow in the original main flowstream and $(1/\beta - 1)$ is the volumetric ratio of gas to liquid flow which may be determined from the densitometer 74, the known specific heat of the gas or vapor, $C_v$ and a selected technique for determining $\beta$ as previously described herein.

$$M(XC_o + (1-X)C_w)(T_{23} - T_{24}) = F_L[XC_o + (1-X)C_w + (1/\beta - 1)(d_v/d_L)C_v](T_{25} - T_{23})$$

This heat balance equation (20) may be solved for the liquid flow, $F_L$. Moreover, the fraction of oil and water in gas may thus be determined from the following equations.

$$F_o = XF_L \qquad (21)$$

$$F_w = (1-X)F_L \qquad (22)$$

$$F_v = (1/\beta - 1)(d_v/d_L)F_L \qquad (23)$$

The system 150 has the advantage of, for a given volumetric flow rate of the main flow stream, a reduced size for the heat exchanger 162. For example, for a well producing 3000 pbd of three phase fluid a shell and tube type heat exchanger having a tube area of about 80 ft² would be required to reduce the temperature of the stream by 5° F., using cooling water with a 50° F. differential. This could be provided in a heat exchanger having about an 8.0 inch diameter by about 8.0 foot length with a coefficient of 50 BTU/ft.²/hr/°F. Pressure differential gauges 157 and 159 may be provided in conduit 156 which is of known cross sectional flow area, for making confirming measurements of total flow-rate.

All of the embodiments of the system of the present invention may be modified to include suitable flow rate, temperature, pressure and density measurement devices having output signal generating capability such that the respective flow rates may be automatically calculated and recorded by suitable computing and recording means, not shown.

Although preferred embodiments of the present invention have been described in detail herein, those skilled in the art will recognize that various substitutions and modifications may be made to the specific apparatus and methods disclosed without departing from the scope and spirit of the invention as recited in the appended claims.

What is claimed is:

1. A system for determining the flow rate of the components of a multiphase fluid flowstream such as being produced from a subterranean hydrocarbon formation, said fluid flowstream comprising primarily crude oil, water and gas, said system including:

conduit means for receiving a main fluid flowstream from said formation and for conducting said main flowstream to a destination;

means interposed in said conduit means for withdrawing a substantially uniform mixture of the liquid as a sample flowstream of said main flowstream;

means for receiving said sample flowstream for determining the composition of said sample flowstream;

heat exchanger means for receiving said main flowstream and for conducting said main flowstream in heat exchange relationship with a heat exchange fluid of known flow/rate; and temperature sensing means for sensing the temperature differential of said main flowstream through said heat exchanger means and the temperature differential of said heat exchange fluid as a result of being conduced in heat exchange relationship with said main flowstream for determining the flowrate of liquid in said main flowstream.

2. The system set forth in claim 1 including:
means for separating gas from said main flowstream and means for reintroducing said separated gas to said main flowstream in said conduit means.

3. The system set forth in claim 2 including:
temperature sensor means for measuring the temperature differential of said main flowstream before separation of said gas and after reinjection of said gas, and temperature sensing means for measuring the temperature differential of said main flowstream before reinjection of said gas for determining the flow rate of said gas in said main flowstream.

4. The system set forth in claim 3, wherein:
said means for separating comprises separator means interposed in said conduit means for separating liquid from said gas, said separator means being interposed in the flow path of said main flowstream upstream in the direction of flow of said fluid from said means for withdrawing said liquid sample.

5. The system set forth in claim 4 wherein:
said means for withdrawing said liquid sample includes means disposed for collecting a liquid sample representative of a uniform mixture of the components of said liquid mixture in said separator means.

6. The system set forth in claim 4 wherein:
said separator means includes a generally cylindrical vessel having a tangential inlet opening for receiving fluid flow from said conduit means, a conduit for conducting vapor away from said separator vessel and a conduit for conducting the liquid mixture of said fluid flowstream away from said separator vessel to said means for determining the composition of said sample flowstream.

7. The system set forth in claim 6 wherein:
said means for withdrawing said liquid sample includes a conduit having a plurality of openings spaced apart radially with respect to a longitudinal axis of said cylindrical vessel for collecting a sample of liquid representative of the mixture of liquids in said fluid flowstream.

8. The system set forth in claim 2 wherein:
said means for separating includes orifice means for distributing liquid and gas within a portion of said conduit means and an array of collector tubes disposed downstream of said orifice means for collecting liquid from said fluid flowstream, said collector tubes being connected to a conduit for conveying collected liquid to a separator vessel, said separator vessel including means for separating gas remaining with said liquid mixture.

9. The system set forth in claim 1 including:
means for determining the specific heat of the liquid in said sample flowstream.

10. The system set forth in claim 9, including:
second heat exchanger means, and means for delivering a predetermined flow rate of liquid sample to said second heat exchanger means.

11. The system set forth in claim 10 wherein:
said second heat exchanger means includes means for adding a predetermined quantity of heat to said sample flowstream at a predetermined rate for measuring the volumetric fraction of oil in said liquid mixture based at least in part on the rate of heat input to said sample flowstream and the increase in temperature of said sample flowstream.

12. The system set forth in claim 10, including:
means for conducting a known flow rate of a known heat exchange fluid to said second heat exchanger means and temperature sensing means for measuring the temperature change of said sample flowstream and said heat exchange fluid.

13. The system set forth in claim 9 including:
means for measuring the density of said main flowstream.

14. The system set forth in claim 1 wherein:
said heat exchanger means includes a source of heat exchange liquid comprising one of the liquids of said fluid flowstream, and means for injecting a measured quantity of said heat exchange liquid into said main flowstream.

15. The system set forth in claim 1 wherein:
said system includes means for determining the water fraction in said liquid mixture by measuring the change in frequency of a microwave signal being propagated through a conductor wherein said liquid mixture comprises a dielectric material interposed between two conductive elements of said conductor.

16. A system for determining the flow rate of the components of a multiphase fluid flowstream such as being produced from a subterranean hydrocarbon formation, said fluid flowstream comprising primarily crude oil, water and gas, said system including:

conduit means for receiving a main fluid flowstream from said formation and for conducting said main flowstream to a destination;

means interposed in said conduit means for withdrawing a substantially uniform mixture of the liquid as a sample flowstream of said main flowstream;

means for passing said sample flowstream in heat exchange relationship with a first heat exchanger means;

second heat exchanger means for conducting said main flowstream in heat exchange relationship with a heat exchange fluid of known quantity;

means for determining the flow rate of said sample flowstream flowing through said first heat exchanger means;

temperature sensing means arranged with respect to said sample flowstream for sensing the temperature differential of said sample flowstream across said first heat exchanger means; and temperature sensing means arranged with respect to said main flowstream for sensing the temperature differential of said main flowstream and said heat exchange fluid through said second heat exchanger means to determine the total liquid flow rate and the total flow rate of one of the liquids of the liquid mixture.

17. A system for determining the flow rate of the components of a multiphase fluid flowstream such as being produced from a subterranean hydrocarbon formation, said fluid flowstream comprising a liquid mixture of primarily crude oil and water and a gas, said system including:

conduit means for receiving a main fluid flowstream from said formation and for conducting said main flowstream to a destination;

means interposed in said conduit means for withdrawing a substantially uniform mixture of said liquid as a sample flowstream of said main flowstream;

heat exchanger means for conducting a heat exchange fluid of known flow rate in heat exchange relationship with said sample flowstream;

means for reinjecting said sample flowstream into said main flowstream at a point upstream of said means for withdrawing said liquid;

means for determining the flow rate of said sample flowstream flowing through said heat exchanger means;

temperature sensing means arranged with respect to said sample flowstream for sensing the temperature differential of said sample flowstream across said heat exchanger means; and temperature sensing means arranged with respect to said main flowstream for sensing the temperature differential of said main flowstream between a point upstream of said point of injection and said means for withdrawing said liquid for determining the total liquid flow rate and the total flow rate of one of the liquids of the liquid mixture.

18. The system set forth in claim 17 wherein:
said means for determining said flow rate of said sample flowstream comprises a mass flowmeter and a volumetric flowmeter.

19. The system set forth in claim 18 wherein:
said mass flowmeter comprises an orifice of known flow area and means for measuring a differential pressure across said orifice of said sample flowstream.

20. A method for determining the flow rate of components of a multiphase fluid flowstream such as a fluid flowstream being produced from a subterranean hydrocarbon formation and wherein said fluid flowstream comprises at least two liquid compositions and a gas all mixed together, said method including the steps of:

withdrawing a sample of the fluid flowstream from time to time to determine the actual composition of the liquids and gas;

providing conduit means for conducting said fluid flowstream, said conduit means including a first heat exchanger for exchanging heat with a main flowstream of said fluid and means for withdrawing on a substantially continuous basis a liquid sample of said fluid flowstream and a second heat exchanger for exchanging heat with said liquid sample;

conducting said main flowstream through said first heat exchanger and measuring the temperature difference of said main fluid flowstream as determined by heat exchange with a known quantity of a known heat exchange fluid;

conducting said sample flowstream through said second heat exchanger and measuring the heat exchanged with said sample flowstream to determine the specific heat of the liquid of said fluid flowstream; and measuring the liquid flow rate based on the flowrate of a heat exchange fluid, the specific heat of the heat exchange fluid, a temperature difference of the main flowstream flowing through said first heat exchanger means and the specific heat of the liquid mixture of said main flowstream.

21. The method set forth in claim 20, including the step of:

separating gas from said fluid flowstream before passing said main flowstream in heat exchange relationship with said heat exchange fluid;

reinjecting said gas into said main flow stream;

measuring the temperature change of said main flowstream resulting from reintroduction of said gas to said main flowstream and measuring the temperature change of said main flowstream resulting from exchanging heat with said heat exchange fluid to determine the flowrate of gas in said main flowstream.

22. The method set forth in claim 20, including the step of:

determining the fraction of oil and water in said main flowstream by passing a sample of said liquid mixture at known flowrate through said second heat exchanger in heat exchange relationship with a heat exchange fluid of known flowrate and measuring the temperature change of said sample of said liquid mixture and said heat exchange fluid to determine the specific heat of said liquid mixture, and comparing the specific heat of said liquid mixture with the specific heat of the components of said liquid mixture.

23. The method set forth in claim 20, including the step of:

determining the volumetric fraction of one of oil and water in said liquid mixture by passing said sample flowstream through said second heat exchanger comprising means for adding heat to said sample flowstream, measuring the temperature differential incurred by a known volumetric flowrate of said sample flowstream when being passed through said second heat exchanger and determining the energy added to said sample flowstream for determining the specific heat of said liquid mixture.

24. The method set forth in claim 20, including the step of:
determining the flowrate of liquid in said fluid flowstream by exchanging heat of said flowstream with a heat exchange liquid using a heat exchanger in which said heat exchange liquid and said flowstream do not mix and comparing the temperature differential across said heat exchanger of both said heat exchange fluid flowstream and said main flowstream.

25. The method set forth in claim 20, including the step of:
determining the flowrate of liquid in said fluid flowstream by injecting a known quantity of a known liquid into said main flowstream, measuring the temperature difference undergone by said main flowstream as a result of injection of said liquid and measuring the temperature difference of said injected liquid.

26. A method for determining the flowrate of the liquid component and the gas component of a multi-phase gas-liquid mixture flowing from a source of said mixture and wherein the composition of the components of said liquid and said gas is known, comprising the steps of:
conducting said multiphase flowstream through a conduit means from said source;
measuring the average density of said multiphase flowstream using density measuring means; and
determining the flowrate of liquid in said main flowstream by passing at least said liquid of said main flowstream in heat exchange relationship with a heat exchange fluid of known flowrate and composition and determining the flowrate of liquid from the change in temperature of the main flowstream and the heat exchange fluid, respectively.

27. The method set forth in claim 26, including the step of:
determining the fraction of one of oil and water in said liquid by passing a sample of said liquid through a conductor for radio frequency electromagnetic radiation and reading the change in transmissivity of said radiation for comparing the change in transmissivity based on known characteristics of said radiation transmissivity for a given percentage of one of said oil and water in the other.

28. The method set forth in claim 26 including the steps of:
withdrawing a sample of uniform mixture of liquid from said main flowstream at a known flowrate of said sample;
passing said sample of known flowrate through heat exchange means to change the temperature of said sample, and measuring the temperature change of said sample in said heat exchange process to determine the specific heat of said sample.

29. A method for determining the flow rate of the liquid component and the gas component of a multi-phase gas-liquid flowstream wherein the composition of the components of said liquid and said gas is known, comprising the steps of:
conducting said multi-phase flowstream through a conduit means from a source of said gas-liquid flowstream;
separating a sample flowstream of liquid from said multi-phase flowstream and passing said sample flow stream through means for measuring the volumetric flow rate and the mass flow rate of said sample flowstream;
passing said sample flowstream through heat exchanger means having a source of cooling fluid of known composition and flow rate and measuring the temperature change of said cooling fluid and said sample flowstream across said heat exchanger means to determine the weight fraction of one of the liquids in said sample flowstream;
re-injecting said sample flowstream into said multi-phase fluid flowstream;
measuring the temperature difference of said multi-phase fluid flowstream between a point upstream of the point of re-injection of said sample flowstream and a point downstream of the point of re-injection of said sample flowstream; and
determining the volumetric flow rate of liquid in the multi-phase fluid flowstream from the mass flow rate of the multi-phase fluid flowstream, the temperature difference of the sample flowstream across said heat exchanger means and the temperature difference of said multi-phase fluid flowstream between the point of re-injection of said sample flowstream and the point of separation of said sample flowstream from said multi-phase fluid flowstream.

* * * * *